US00PP25972P3

(12) United States Plant Patent
Lugli et al.

(10) Patent No.: US PP25,972 P3
(45) Date of Patent: Oct. 6, 2015

(54) CHERRY TREE NAMED 'PA5UNIBO'

(50) Latin Name: *Prunus avium*
Varietal Denomination: PA5UNIBO

(71) Applicant: Alma Mater Studiorum-Università degli Studi di Bologna, Bologna (IT)

(72) Inventors: Stefano Lugli, Modena (IT); Riccardo Correale, Bologna (IT); Michelangelo Grandi, Castenaso (IT)

(73) Assignee: Alma Mater Studiorum-Università degli Studi di Bologna, Bologna (IT)

( * ) Notice: Subject to any disclaimer, the term of this patent is extended or adjusted under 35 U.S.C. 154(b) by 122 days.

(21) Appl. No.: 13/986,686

(22) Filed: May 24, 2013

(65) Prior Publication Data

US 2014/0033377 P1 Jan. 30, 2014

(30) Foreign Application Priority Data

May 25, 2012 (QZ) ..... PBR 20121161

(51) Int. Cl.
*A01H 5/00* (2006.01)
*A01H 5/08* (2006.01)

(52) U.S. Cl.
USPC ..... Plt./181
CPC ..... *A01H 5/085* (2013.01)

(58) Field of Classification Search
USPC ..... Plt./181
See application file for complete search history.

(56) References Cited

PUBLICATIONS

PLUTO Plant Variety Database Dec. 2, 2014. p. 1. Search for PA5UNIBO.*

* cited by examiner

*Primary Examiner* — Annette Para
(74) *Attorney, Agent, or Firm* — Hershkovitz & Associates, PLLC; Abraham Hershkovitz

(57) ABSTRACT

'PA5UNIBO' is a novel cherry tree derived from a seedling of unknown cross which was planted at Vignola, Modena Province, Italy. The genus and species (cultivar) of 'PA5UNIBO' is *Prunus avium*. It was initially propagated by grafting to root stocks of varying vigor and, after testing in districts and plantings of differing types, proved to have the qualities proper to a promising new cultivar for the market.

5 Drawing Sheets

Latin name of the genus/species of the plant claimed (cultivar): *Prunus avium.*

Variety denomination: PA5UNIBO.

CROSS-REFERENCE TO RELATED APPLICATIONS

Priority is claimed of the pending EU Plant Patent for 'PA5UNIBO', which was filed on 25 May 2012 as Application No. 2012/1161 in the name of Applicant (holder) Alma Mater Studiorum—University of Bologna, the entire contents of which is expressly incorporated herein by reference. EU Trademark for 'Sweet Saretta' was released on 2 Jan. 2013 as Registration No. 011058691 of Applicant (holder) Alma Mater Studiorum—University of Bologna. Such European Trademark is associated to PA5UNIBO and used to distinguish such cherry variety from the others.

BACKGROUND OF THE INVENTION

'PA5UNIBO' named 'Sweet Saretta', derived from seedling of unknown cross and originally called Selection DCA BO B5A87, was planted at Vignola, Modena Province, Italy, in February 2002 and first cropped in 2004. It was initially propagated by grafting to root stocks of varying vigor and, after testing in districts and plantings of differing types, proved to have the properties proper to a promising new cultivar for the market. It picks in the second decade to the end of June, about 22-24 days after early known cultivars such as 'Burlat' (and about 6 days after 'Bing', but before known later harvest types such as 'Lapins'.

BRIEF SUMMARY OF THE INVENTION

The parentage of the variety is unknown. The name of a known variety for comparison to comparable harvest date is 'Sylvia'. However, compared to 'Sylvia', *Prunus avium* 'PA5UNIBO' has larger fruit of firmer flesh, more uniform ripening and higher sugar content. The fruit is comparable in size to 'Duroni 3' and 'Sunburst' varieties, and the prevailing caliber is 30-32 mm. 'PA5UNIBO' was selected for its high qualities, including tree growth and yield performance, fruit appearance (bright red, scale 4 CTIFL), with excellent taste-flavor properties, aromatic and very sweet with a good level of acidity. The distinctive traits of 'PA5UNIBO' also include mid-to-late picking date, uniform ripening, and high field performance. The date of cross was in the year 2000. The location of the discovery was Vignola, Modena Province, Italy. The date of the first asexual propagation was in 2008 in Vignola, Modena Province, Italy. 'PA5UNIBO' resulted from a cross of unknown varieties, but was initially propagated on root stock of 'Gisela 6' (U.S. Plant Pat. No. 8,954) in the trial fields of Bologna University to test field and cropping performance in a medium-to-high density planting.

BRIEF DESCRIPTION OF THE DRAWINGS

The accompanying photographs show typical specimens of the new variety as depicted in color as nearly true as is reasonably possible in color illustrations of this character.

DETAILED BOTANICAL DESCRIPTION OF THE VARIETY

Figure 1:
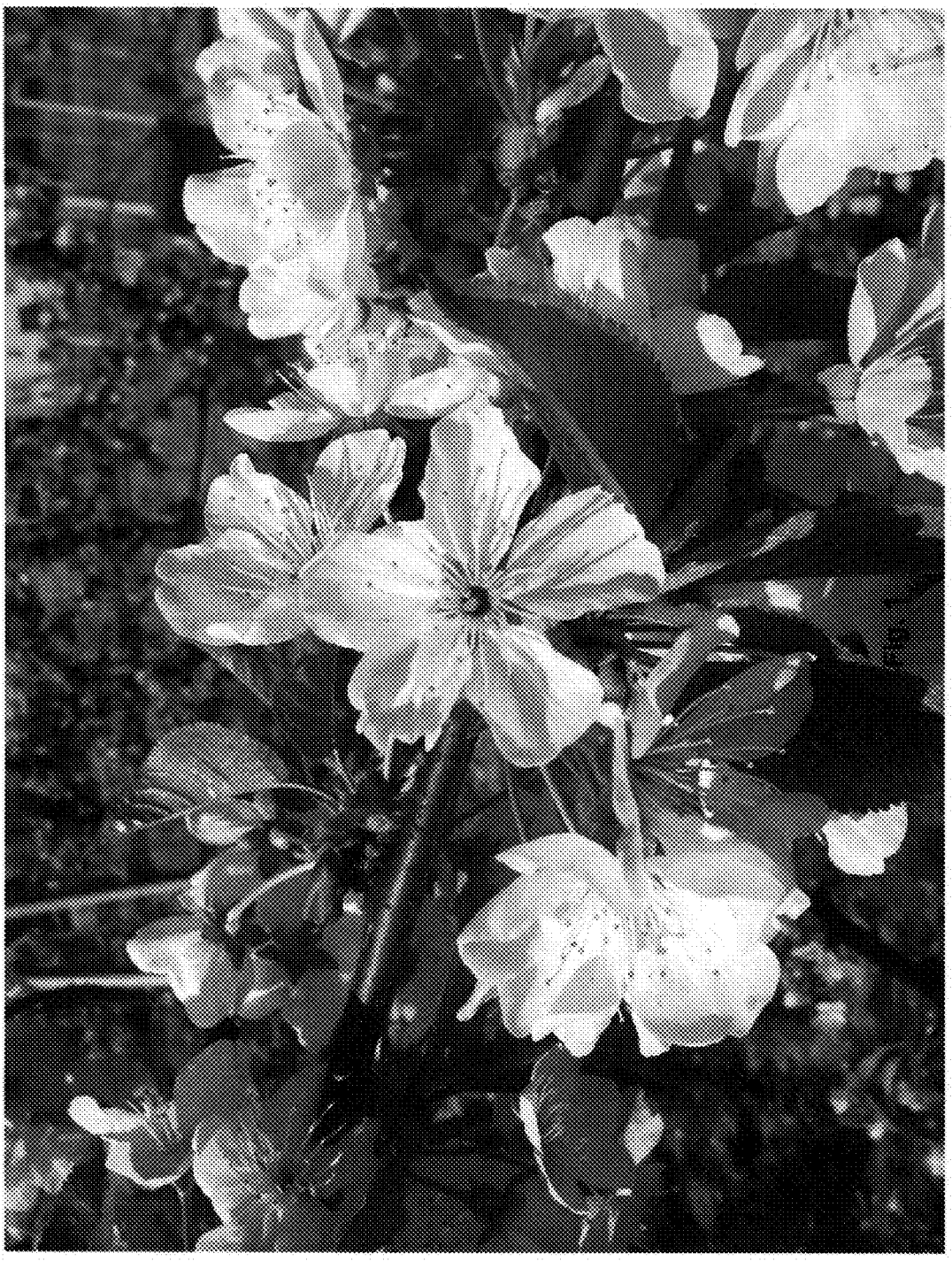
FIG. 1 illustrates the detail of fully-open blossoms of PA5UNIBO.
Figure 2:
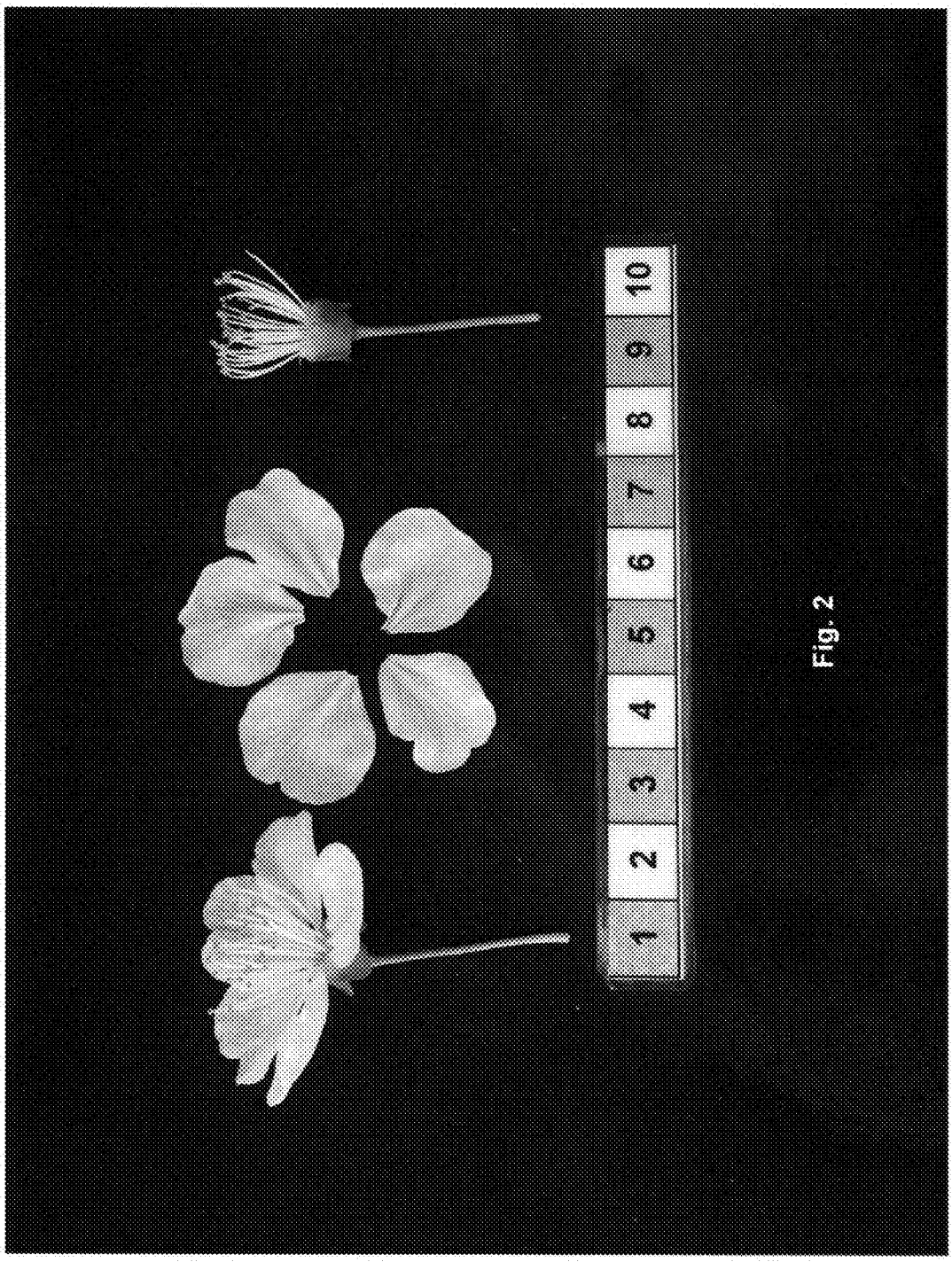
FIG. 2 is the flower, full front, in profile and with separated petals, of PA5UNIBO.
Figure 3:
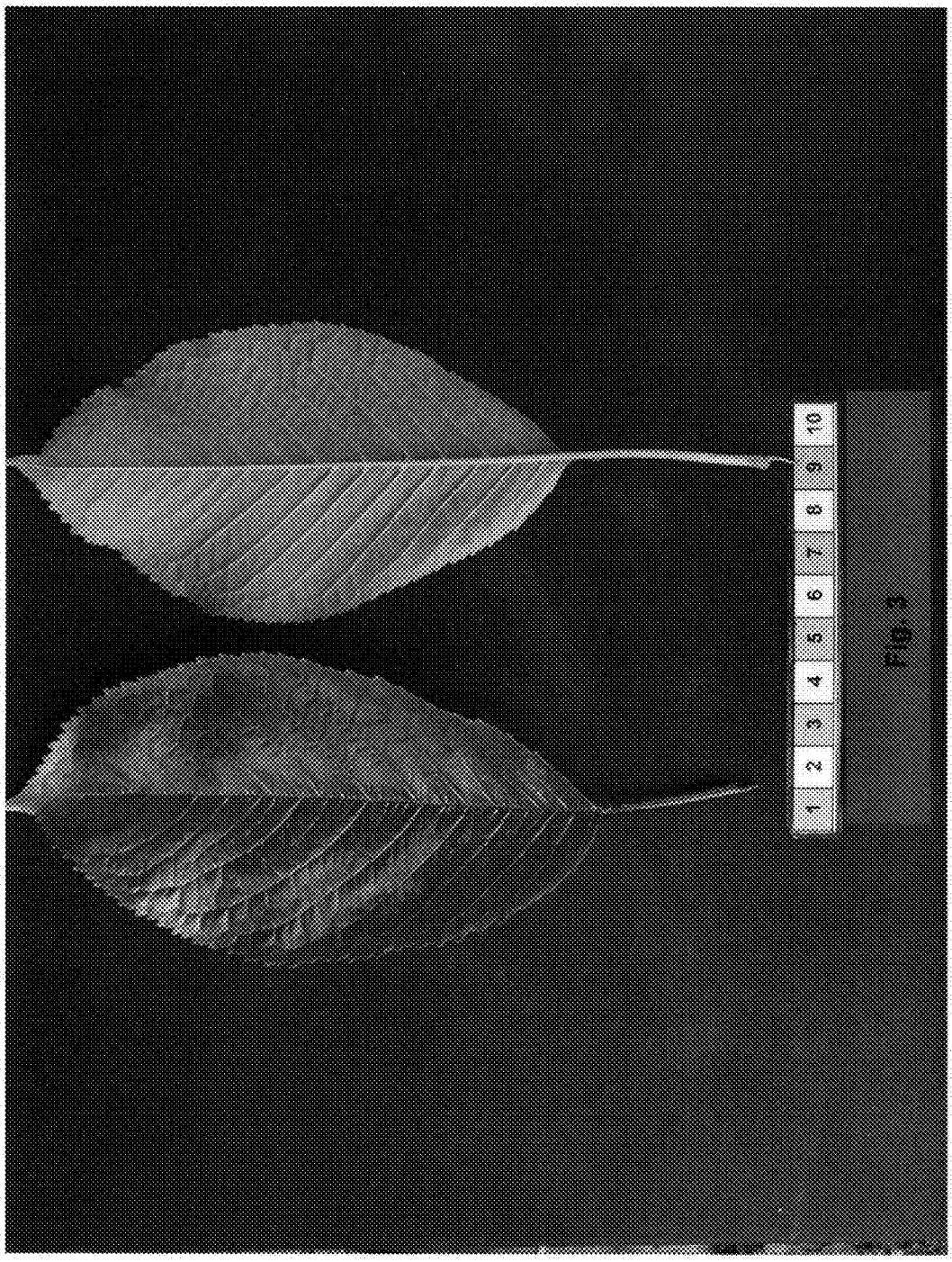
FIG. 3 shows the leaf profile of PA5UNIBO. Two leaves have been detached and one has been placed upper leaf surface side down to show the lower leaf surface details.
Figure 4:
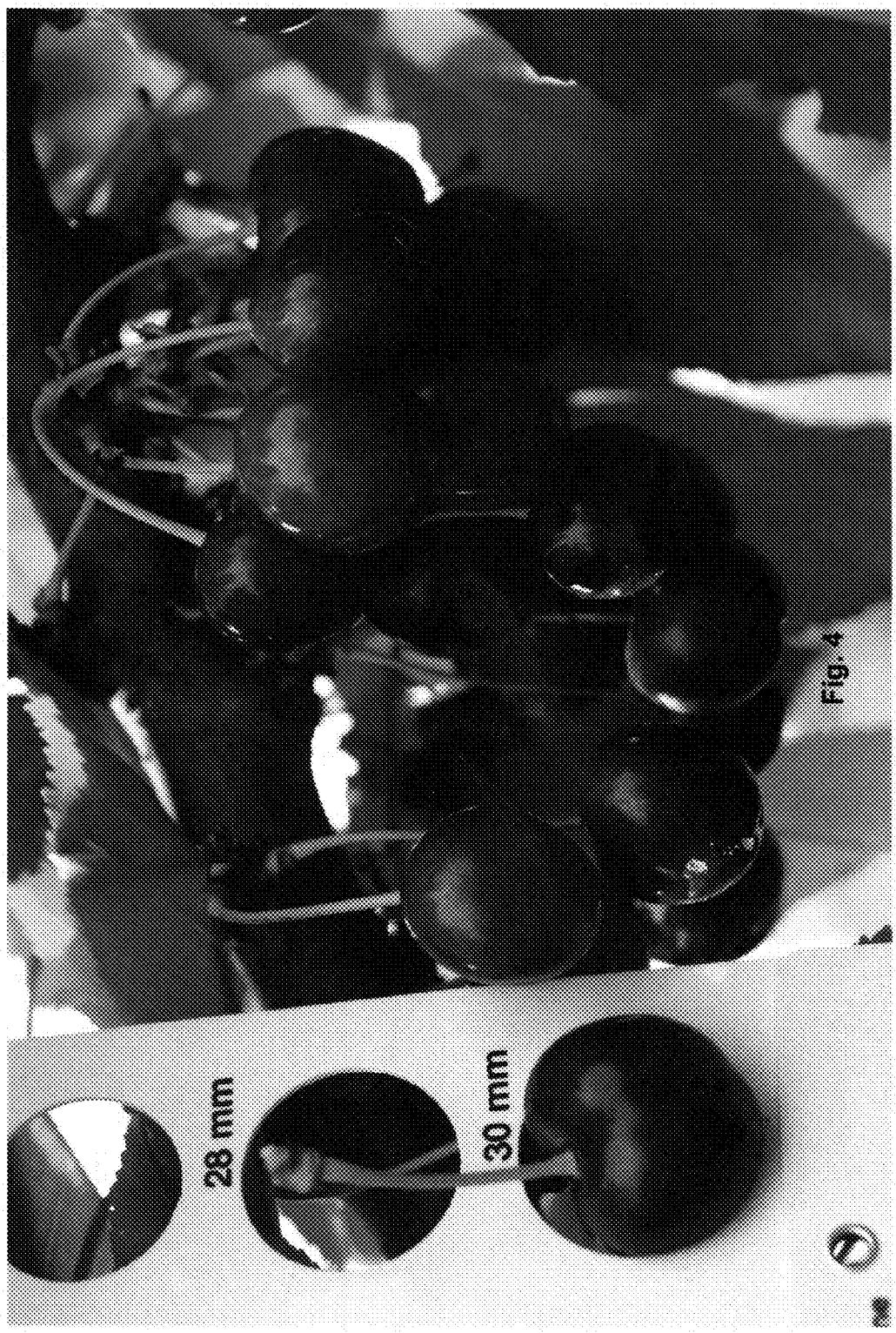
FIG. 4 illustrates the details of a fruit cropping, including an example measurement, of PA5UNIBO.
Figure 5:
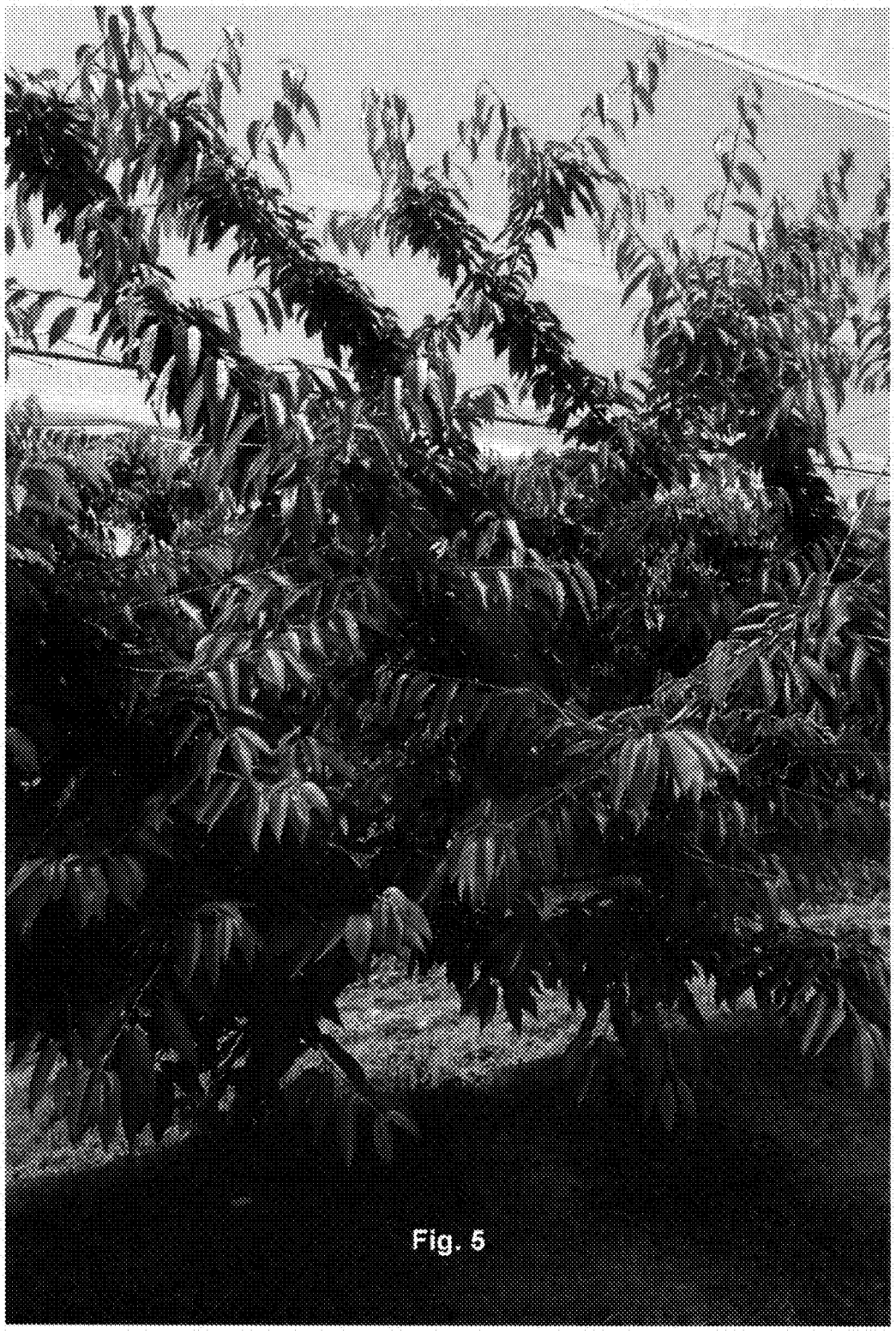
FIG. 5 shows the tree architecture of PA5UNIBO with width-spread and height.

General:

*Age of described tree(s).*—5 years, slender spindle training system.

*Location of described trees(s).*—Vignola, Modena Province, Italy.

*Name of color chart used.*—The Royal Horticultural Society Colour Chart.

*Name of root stock.*—'Gisela 6'.

Tree:

*Vigor.*—High.

*Height.*—3.5-4 meters.

*Spread.*—3 meters.

*Growth habit.*—Open canopy.

*Canopy density.*—Medium.

*Trunk diameter at specified height.*—16-17 cm, as measured at about 5 cm above graft joint.

*Trunk color.*—Dark reddish-brown (200A).

*Bark texture.*—Of average roughness.

*Tendency toward alternate bearing.*—No.

*Winter hardiness.*—Unknown, no winter cold damage found in this Po Valley district.

*Chilling requirement.*—Unknown.

Branch:

*Length.*—160-220 cm of main branches.

*Diameter.*—5-8 cm.

*Crotch angle.*—45-60° depending on training system.

*Bark color.*—Dark reddish-brown (200A).

*Bark texture.*—Of verge roughness.

Current year shoot:

*Length.*—40-60 cm.

*Color.*—Dark reddish-brown (200C/200D) with fairly diffuse gray overtone (201A).

Winter hardiness:

*USDA hardiness zone.*—Unknown.

*Chilling requirement.*—Unknown.

Flower buds:

*Number per spur.*—4-6, mostly 5.

*Shape.*—Ovoid.

*Length.*—About 1 cm.

*Diameter.*—Under 1 cm.

*Color.*—Reddish perules (187C).

Flowers:

*Number per cluster.*—Minimum 7-maximum 11 per spur, 2-3 per bud. Abundant bloom.

*Relative position of petals.*—Slightly overlapping petals.

*Diameter.*—38-40 mm.

*Depth.*—16-18 mm, as measured from receptacle to maximum petal aperture.

*Is pollen produced?.*—Yes.

*Coloration of pollen.*—Yellow (13A).

Sepal:

*Length.*—6-7 mm.

*Shape.*—Conical.

*Width.*—About 5 mm.

*Apex.*—Pointed.

*Base.*—Pointed.

*Margin descriptors.*—Regular margin. Color — upper surface: Green (139C). Color — lower surface: Pale green (138C).

Petals:

*Number per flower.*—5.

*Shape.*—Circular.

*Length.*—16-19 mm.

*Width.*—16-17 mm.

*Apex.*—Slightly sunken.

*Base.*—Slightly pointed.

*Margin.*—Slightly undulated. Color — upper surface White (155B). Color — lower surface White (155B).

Bloom:

*Date of bud burst.*—7-8 Apr. 2013.

*Date of first bloom.*—13 Apr. 2013.

*Date of full bloom.*—16 Apr. 2013.

Pedicel:

*Length.*—26-34 mm.

*Diameter.*—1.2-1.4 mm.

*Color.*—Green (143B).

Pistil:

*Quantity.*—1.

*Size.*—15-19 mm.

*Color.*—Green (143C).

Anthers:

*Quantity.*—26-30 of 5-15 mm length; many anthers in each flower are at the same height as the stigma and some exceed it. White filament (155D).

*Size.*—Under 1 mm diameter.

*Color.*—Yellow (15C).

Stigma:

*Quantity.*—1.

*Size.*—About 1 mm.

*Color.*—Green (142A).

Styles:

*Quantity.*—1.

*Size.*—12-14 mm length.

*Color.*—Pale-white-green (142C) tending toward rosé (36C) at end of bloom.

Ovary/ies:

*Quantity.*—1.

*Size.*—3-5 mm.

*Color.*—Green (143C).

Leaves:

*Length.*—13.7-15.8 cm.

*Width.*—6.7-9.1 cm.

*Shape.*—Elliptical.

*Apex shape.*—Pointed.

*Base shape.*—Pointed.

*Margin.*—Fine-toothed. Color — upper surface: Dark green (137A/137B). Color — lower surface: Pale green (138B) with green-yellow central vein (152A/152B).

Petiole:

*Length.*—3.4-4.6 cm.

*Diameter.*—About 2 mm.

*Color.*—Green-yellow (152A/152B) under and reddish upper (183A).

Fruit:

*Shape.*—Heart-shaped.

*Diameter.*—Mostly 30-32 mm.

*Height.*—26-28 mm.

*Weight.*—11-12 grams, average weight.

*Number per cluster.*—6-9 per spur.

*Skin color* (*include ground color and over color*).—Bright red (N186C) tending toward bright vermilion red (N186B) at advanced maturity.

*Presence of lenticels.*—Yes.

*Density of lenticels.*—Medium.

*Skin thickness.*—Medium-thin.

*Skin texture.*—Medium.

*Anthocyanin coloration present near skin?.*—No.

*Tenacity of flesh to stone.*—Low.

*Flesh color.*—Red (53A).

*Flesh texture.*—Fine.

*Juiciness.*—High.

*Juice analysis* (*brix, acidity, tss, etc.*).—18.5° Brix and 7.8 g/l malic acid (2012 data).

*Stone size.*—Medium.

*Stone shape.*—Elliptical.

*Stone color.*—Pale brown (165D).

Fruit stem:

*Length.*—36-39 mm.

*Diameter.*—Just over 1 mm.

*Color.*—Green (143B).

Harvest:

*Maturity date range.*—June 10-June 30, approximately 22-24 days after 'Burlat' and about 4-6 days after optimum US harvest dates of June 15-June 20 for 'Bing'.

*Harvest date range* (*if different*).—Same as above.

'PA5UNIBO' is a diploid cultivar and is self-fertile (S3S4' alleles). Fruit load and yield have always been high and consistent, particularly in presence of flying insects (e.g., bees, wasps, hornets, beetles and butterflies).

Under observation during planting, growing and harvesting under normal cultural and growing conditions in Modena Province, Italy, no particular insect or plant/fruit disease resistance or susceptibility has been observed.

Because of the outstanding and unique horticultural characters of the claimed plant, especially its long harvest period and large size, this cherry can be planted to extend the cultivar's season. Although this new variety of cherry possesses the above-described characteristics, it is to be understood that variations and fluctuations may occur in the magnitude and qualities due to changes in growing and climate conditions, irrigation, fertilization, pruning and pest control.

What is claimed is:

1. A new and distinct cherry tree as herein described and illustrated.

* * * * *